United States Patent
Gerhard et al.

(10) Patent No.: US 7,527,798 B2
(45) Date of Patent: May 5, 2009

(54) COMPOSITION AND METHOD FOR PREVENTING OR TREATING A VIRUS INFECTION

(75) Inventors: Walter Gerhard, Philadelphia, PA (US); Laslo Otvos, Audubon, PA (US)

(73) Assignee: The Wistar Institute, Philadelphia, PA (US)

( * ) Notice: Subject to any disclaimer, the term of this patent is extended or adjusted under 35 U.S.C. 154(b) by 282 days.

(21) Appl. No.: 10/541,771

(22) PCT Filed: Jan. 14, 2004

(86) PCT No.: PCT/US2004/000899

§ 371 (c)(1),
(2), (4) Date: Nov. 30, 2005

(87) PCT Pub. No.: WO2004/064784

PCT Pub. Date: Aug. 5, 2004

(65) Prior Publication Data

US 2006/0171961 A1    Aug. 3, 2006

(51) Int. Cl.
*A61K 39/385* (2006.01)
*A61K 39/145* (2006.01)
*C07K 17/00* (2006.01)

(52) U.S. Cl. ............... 424/193.1; 424/196.11; 424/209.1; 530/403

(58) Field of Classification Search ............ None
See application file for complete search history.

(56) References Cited

OTHER PUBLICATIONS

Kragol et al (Bioorganic & Medicinal Chemistry Letters 11:1417-1420, 2001).*
Kragol et al (Bioorganic & Medicinal Chemistry Letters 11:1417-1420, 2001, cited in IDS).*
Neirynck et al (Nature Medicine 5:1157-1163, 1999, cited in IDS).*
Kragol et al.: Orthogonal Solid-Phase Synthesis of Tetramannosylated Peptide Constructs Carrying Three Independent Branched Epitopes, Tetrahedron 57 (2001) 957-966.
Kragol et al.: Synthesis of a Disulfide-Linked Octameric Peptide Construct Carrying Three Different Antigenic Determinants, Bioorganic & Medicinal Chemistry Letters 11 (2001) 1417-1420.
Mozdzanowska et al.: Induction of Influenza Type A Virus-Specific Resistance by Immunization of Mice With a Synthetic Multiple Antigenic Peptide Vaccine That Contains Ectodomains of Matrix Protein 2, Vaccine 21 (2003) 2616-2626.
Neirynck et al.: A Universal Influenza A Vaccine Based on the Extracellular Domain of the M2 Protein, Nature Medicine, vol. 5, No. 10, Oct. 1999.

* cited by examiner

*Primary Examiner*—Mary E Mosher
(74) *Attorney, Agent, or Firm*—Licata & Tyrrell P.C.

(57) ABSTRACT

The present invention provides multiple antigenic agents compositions and the use thereof to prevent or treat viral infections.

15 Claims, No Drawings

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (1)..(1)
<223> OTHER INFORMATION: N-terminal amino group has attached R1 which is
      0 to 2 amino acid residues, wherein said amino acid residue may be
      a Gly or Cys,     or a nucleic acid sequence.
<220> FEATURE:
<221> NAME/KEY: MISC_FEATURE
<222> LOCATION: (1)..(1)
<223> OTHER INFORMATION: Side chain amino group has attached R2 which is
      a B cell determinant, a T cell determinant, or a targeting
      molecule.
<220> FEATURE:
<221> NAME/KEY: MISC_FEATURE
<222> LOCATION: (3)..(3)
<223> OTHER INFORMATION: Side chain amino group has attached R3 which is
      a B cell determinant, a T cell determinant, or a targeting
      molecule.
<220> FEATURE:
<221> NAME/KEY: MISC_FEATURE
<222> LOCATION: (5)..(5)
<223> OTHER INFORMATION: "Xaa" represents 0 to 1 amino acid residue of
      Lys-R4, wherein R4 is a B cell determinant, a T cell determinant,
      or a targeting molecule.
<220> FEATURE:
<221> NAME/KEY: MISC_FEATURE
<222> LOCATION: (5)..(5)
<223> OTHER INFORMATION: C-terminus has attached R5 group which is an
      amino acid, peptide, or nucleic acid sequence.

<400> SEQUENCE: 1

Lys Gly Lys Gly Xaa
1               5

<210> SEQ ID NO 2
<211> LENGTH: 14
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (1)..(1)
<223> OTHER INFORMATION: Mannosylated residue
<220> FEATURE:
```

```
<221> NAME/KEY: MISC_FEATURE
<222> LOCATION: (2)..(2)
<223> OTHER INFORMATION: Mannosylated serine residue attached to side
      chain amino group
<220> FEATURE:
<221> NAME/KEY: MISC_FEATURE
<222> LOCATION: (4)..(4)
<223> OTHER INFORMATION: Mannosylated serine residue attached to side
      chain amino group
<220> FEATURE:
<221> NAME/KEY: MISC_FEATURE
<222> LOCATION: (6)..(6)
<223> OTHER INFORMATION: Mannosylated serine residue attached to side
      chain amino group
<220> FEATURE:
<221> NAME/KEY: MISC_FEATURE
<222> LOCATION: (8)..(8)
<223> OTHER INFORMATION: S2 peptide attached to side chain amino group
<220> FEATURE:
<221> NAME/KEY: MISC_FEATURE
<222> LOCATION: (10)..(10)
<223> OTHER INFORMATION: S1 peptide attached to side chain amino group
<220> FEATURE:
<221> NAME/KEY: MISC_FEATURE
<222> LOCATION: (12)..(12)
<223> OTHER INFORMATION: M2e peptide attached to side chain amino group

<400> SEQUENCE: 2

Ser Lys Gly Lys Gly Lys Gly Lys Gly Lys Gly Lys Gly Ala
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (3)..(3)
<223> OTHER INFORMATION: Serine attached to side chain amino group
<220> FEATURE:
<221> NAME/KEY: MISC_FEATURE
<222> LOCATION: (5)..(5)
<223> OTHER INFORMATION: Serine attached to side chain amino group
<220> FEATURE:
<221> NAME/KEY: MISC_FEATURE
<222> LOCATION: (7)..(7)
<223> OTHER INFORMATION: S2 peptide attached to side chain amino group
<220> FEATURE:
<221> NAME/KEY: MISC_FEATURE
<222> LOCATION: (9)..(9)
<223> OTHER INFORMATION: S1 peptide attached to side chain amino group
<220> FEATURE:
<221> NAME/KEY: MISC_FEATURE
<222> LOCATION: (11)..(11)
<223> OTHER INFORMATION: M2e peptide attached to side chain amino group

<400> SEQUENCE: 3

Lys Gly Lys Gly Lys Gly Lys Gly Lys Gly Lys Gly Ala
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (2)..(2)
<223> OTHER INFORMATION: Serine residue attached to side chain
<220> FEATURE:
<221> NAME/KEY: MISC_FEATURE
<222> LOCATION: (4)..(4)
```

```
<223> OTHER INFORMATION: S2 peptide attached to side chain amino group
<220> FEATURE:
<221> NAME/KEY: MISC_FEATURE
<222> LOCATION: (6)..(6)
<223> OTHER INFORMATION: S1 peptide attached to side chain amino group
<220> FEATURE:
<221> NAME/KEY: MISC_FEATURE
<222> LOCATION: (8)..(8)
<223> OTHER INFORMATION: M2e peptide attached to side chain amino group
<220> FEATURE:
<221> NAME/KEY: MISC_FEATURE
<222> LOCATION: (10)..(10)
<223> OTHER INFORMATION: M2e peptide attached to side chain amino group

<400> SEQUENCE: 4

Ser Cys Gly Lys Gly Lys Gly Lys Gly Lys Gly Ala
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (1)..(1)
<223> OTHER INFORMATION: Dimer created by disulfide linkage
<220> FEATURE:
<221> NAME/KEY: MISC_FEATURE
<222> LOCATION: (3)..(3)
<223> OTHER INFORMATION: S2 peptide attached to side chain amino group
<220> FEATURE:
<221> NAME/KEY: MISC_FEATURE
<222> LOCATION: (5)..(5)
<223> OTHER INFORMATION: S1 peptide attached to side chain amino group
<220> FEATURE:
<221> NAME/KEY: MISC_FEATURE
<222> LOCATION: (7)..(7)
<223> OTHER INFORMATION: M2e peptide attached to side chain amino group
<220> FEATURE:
<221> NAME/KEY: MISC_FEATURE
<222> LOCATION: (9)..(9)
<223> OTHER INFORMATION: M2e peptide attached to side chain amino group

<400> SEQUENCE: 5

Cys Gly Lys Gly Lys Gly Lys Gly Lys Gly Ala
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic multiple antigenic agent

<400> SEQUENCE: 6

Cys Gly Lys Gly Lys Gly Lys Ala
    1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic multiple antigenic agent
<220> FEATURE:
<221> NAME/KEY: MISC_FEATURE
<222> LOCATION: (3)..(3)
<223> OTHER INFORMATION: M2e petide attached to side chain amino group
<220> FEATURE:
<221> NAME/KEY: MISC_FEATURE
<222> LOCATION: (5)..(5)
```

```
<223> OTHER INFORMATION: M2e petide attached to side chain amino group

<400> SEQUENCE: 7

Cys Gly Lys Gly Lys Gly Lys Ala
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic S1 peptide

<400> SEQUENCE: 8

Ser Phe Glu Arg Phe Glu Ile Phe Pro Lys Glu
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic S2 peptide

<400> SEQUENCE: 9

His Asn Thr Asn Gly Val Thr Ala Ala Ser Ser His Glu
1               5                   10

<210> SEQ ID NO 10
<211> LENGTH: 24
<212> TYPE: PRT
<213> ORGANISM: Artificial Sequence
<220> FEATURE:
<223> OTHER INFORMATION: Synthetic M2e peptide

<400> SEQUENCE: 10

Ser Leu Leu Thr Glu Val Glu Thr Pro Ile Arg Asn Glu Trp Gly Cys
1               5                   10                  15

Arg Ser Asn Asp Ser Ser Asp Pro
            20
```

COMPOSITION AND METHOD FOR PREVENTING OR TREATING A VIRUS INFECTION

INTRODUCTION

This invention was made in the course of research sponsored by the National Institute of Allergy and Infectious Disease (NIAID Grant Nos. AI-46457 and AI-13989). The U.S. government has certain rights in this invention.

BACKGROUND OF THE INVENTION

Three types of transmembrane proteins are expressed in the membrane of influenza type A virions and virus-infected cells. The hemagglutinin and neuraminidase are glycoproteins with large ectodomains of ~510 and ~420 amino acids, respectively. Hemagglutinin is assembled as homotrimers and neuraminidase as homotetramers forming a dense layer of 13-14 nm long, rod-shaped surface projections on the viral membrane and at cellular sites of virus maturation. Current influenza virus vaccines aim at inducing a strong antibody response to these glycoproteins, particularly the hemagglutinin, as such antibodies are well-known to be highly protective against infection. The problem is that influenza type A virus has a high propensity for changing the determinants recognized by these protective antibodies, which necessitates repetitive vaccination with updated vaccine strains that reflect these antigenic changes. By contrast, the third viral transmembrane protein, matrix protein 2 (M2), contains an ectodomain (M2e) that is highly conserved amongst human influenza virus strains. Broad protective immunity against influenza type A virus infection using M2 has been investigated (Slepushkin, et al. (1995) *Vaccine* 13:1399-1402; Frace, et al. (1999) *Vaccine* 17:2237-44; Neirynck, et al. (1999) *Nature Med.* 5:1157-63; Okuda, et al. (2001) *Vaccine* 19:3681-91).

M2 is a 97 amino acid non-glycosylated transmembrane protein (Lamb, et al. (1981) *Proc. Natl. Acad. Sci. USA* 78:4170-4; Lamb, et al. (1985) *Cell* 40:627-33). It forms homotetramers (Holsinger and Lamb (1991) *Virology* 183:32-43; Sugrue and Hay (1991) *Virology* 180:617-24) that are expressed at low density in the membrane of virus particles (~10 M2 tetramers compared to ~400 hemagglutinin trimers and ~100 neuraminidase tetramers per average virion) but at high density in the plasma membrane of infected cells (similar density as hemagglutinin) (Zebedee and Lamb (1988) *J. Virol.* 62:2762-72). M2-tetramers exhibit pH-inducible proton-transport activity (Steinhauer, et al. (1991) *Proc. Natl. Acad. Sci. USA* 88:11525-9; Pinto, et al. (1992) *Cell* 69:517-28) which appears to facilitate the release of RNP complexes from the viral membrane after fusion (Zhirnov (1990) *Virology* 176:274-9) and prevents an excessive drop of pH within transport vesicles during egress of viral transmembrane proteins from endoplasmic reticulum to the plasma membrane, thereby preventing a premature acid-induced conformational change in hemagglutinin (Steinhauer, et al. (1991) supra). The 23 amino acid long M2e is totally conserved in its nine N-terminal amino acids and shows only a relatively minor degree of structural diversity in its membrane-proximal 15 amino acid long section (Zebedee and Lamb (1988) supra; Ito, et al. (1991) *J. Virol.* 65:5491-8). Amongst human isolates of H1N1, H2N2, H3N2, and H5N1 subtypes, two alternative amino acids have been found at seven positions but the majority of human isolates actually share the same sequence.

M2e-specific monoclonal antibody 14C2 does not prevent virus infection in vitro but reduces virus yield and plaque size when incorporated into the culture medium or agar overlay (Zebedee and Lamb (1988) supra; Hughey, et al. (1995) *Virology* 212:411-21). Not all M2e-specific antibodies display this activity (Hughey, et al. (1995) supra) and not all virus strains are susceptible to it (Zebedee and Lamb (1988) supra). In vivo, passive monoclonal antibody 14C2 similarly decreases virus growth (Treanor, et al. (1990) *J. Virol.* 64:1375-7) and is effective also against PR8 (Mozdzanowska, et al. (1999) *Virology* 254:138-46), which is not susceptible to antibody-mediated growth restriction in vitro (Zebedee and Lamb (1988) supra; Mozdzanowska, et al. (1999) supra), indicating that antibody-mediated virus growth-inhibition occurs through distinct mechanisms in vitro and in vivo.

The protective efficacy of actively induced M2-specific immunity has been tested using various types of vaccine constructs and vaccination modalities. Initial studies, in which mice and ferrets were vaccinated with M2-expressing, recombinant vaccinia virus, showed no evidence of protection (Epstein, et al. (1993) *J. Immunol.* 150:5484-93; Jakeman, et al. (1989) *J. Gen. Virol.* 70:1523-31), although the induction of M2-specific immune responses was not verified. Subsequent studies tested plasmid DNA containing the intact M gene segment (coding for M1 and M2 protein) (Okuda, et al. (2001) supra), an intact recombinant M2 protein membrane preparation (Slepushkin, et al. (1995) supra), an M2 protein with a deleted transmembrane portion (to decrease toxicity and increase solubility) (Frace, et al. (1999) supra), and a construct in which M2e was fused to hepatitis B virus core protein (Neirynck, et al. (1999) supra). These latter vaccination protocols induced protection, both in terms of reduction in virus growth and mortality.

It has now been found that a multiple antigenic agent containing M2e linked to helper T cell determinants is an effective vaccine for inducing virus protection. M2e-MAAs together with cholera toxin (CT) and a synthetic oligodeoxynucleotide (ODN) with a stimulatory CpG motif induces strong M2e-specific antibody titers in serum of mice and results in significant protection against influenza virus challenge.

SUMMARY OF THE INVENTION

One aspect of the present invention is a multiple antigenic agent (MAA) of the structure:

$$R_1-(Lys-Gly)_m-(Lys-Gly)_n-Xaa_1-R_5 \atop \phantom{R_1-(Lys-}|\phantom{Gly)_m-(}|\phantom{Lys-Gly)} \atop \phantom{R_1-(Lys-}R_2\phantom{Gly)_m-(}R_3} \quad \text{Formula I}$$

(SEQ ID NO:1) wherein, $R_1$ is 0 to 2 amino acid residues comprising Cys or Gly or a nucleic acid sequence; m is at least 1; n is at least 1; $Xaa_1$ is 0 to 1 amino acid residue comprising Lys-$R_4$; $R_2$, $R_3$, and $R_4$ may independently be a B cell determinant, a T cell determinant, or a targeting molecule; and $R_5$ is any amino acid, peptide, or nucleic acid sequence. In a preferred embodiment, the B cell determinant is the ectodomain of matrix protein 2 or a homolog thereof. In another preferred embodiment, a Cys residue located at the N-terminus of a first MAA is covalently linked via a disulfide bond to a second Cys residue at the N-terminus of a second MAA of Formula I to produce an MAA dimer of Formula I.

Another aspect of the present invention is a composition containing an MAA and a pharmaceutically acceptable carrier. In a preferred embodiment, the composition containing the MAA and the pharmaceutically acceptable carrier may further contain an adjuvant. Such compositions are useful for preventing or treating a viral infection. Accordingly, a method for preventing or treating a viral infection is provided involving administering to a susceptible subject or one exhibiting signs or symptoms of viral infection an effective amount of a composition of the invention to prevent or treat the signs or symptoms of a viral infection. Preferably, said viral infection is influenza type A virus.

These and other aspects of the present invention are set forth in more detail in the following description of the invention.

DETAILED DESCRIPTION OF THE INVENTION

It has now been found that animals, inoculated with multiple antigenic agents (MAAs) containing multiple B cell determinants and T helper cell (Th) determinants, exhibit significant resistance against subsequent challenge with infectious virus. As defined herein, a multiple antigenic agent is an agent which contains more than one peptide or nucleic acid moiety which is capable of inducing a specific immune response in an animal. The B cell determinant induces an antibody response and may also induces a T cell response. The advantage of the MAAs provided herein is that a multitude of antigenic side chains can be attached to the core peptide which contains Lys-Gly repeats thereby enabling presentation of several structurally linked determinants. Furthermore, when a Cys residue is linked at the N-terminus of the core peptide, two core peptides can be covalently linked via disulfide bonds to effectively double the number of antigenic side chains and hence improve immune responses in mammals. Further, as the MAA provided herein can be readily chemically synthesized, the production of the MAA is highly controlled and contaminants are minimized.

Accordingly, one aspect of the present invention provides an MAA of the structure:

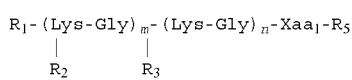

Formula I (SEQ ID NO:1) wherein m is at least 1 and n is at least 1. In a preferred embodiment, the summation of m and n is about 10 to 30, preferably about 10.

In the MAA of Formula I, the amino acid moiety $Xaa_1$ is 0 to 1 amino acid residue, wherein said amino acid residue is Lys-$R_4$.

In the MAA of Formula I, the $R_1$ moiety is 0 to 2 amino acid residues, wherein said amino acid residue may be a Gly or Cys, or a nucleic acid sequence such as an oligodeoxynucleotide (ODN) with a stimulatory CpG motif. In a preferred embodiment, $R_1$ is the dipeptide Cys-Gly. When the N-terminal amino acid of a first MAA is a Cys residue it is preferably covalently linked to a second Cys residue at the N-terminus of a second MAA of Formula I. The disulfide linkage between the first and second cysteine residues generates a covalently linked MAA dimer of Formula I. It is contemplated that the peptides of the dimer may be identical or differ in the number of Lys-Gly repeats (i.e., the number of m and n), $Xaa_1$, $R_2$, $R_3$, $R_4$ or $R_5$.

In the MAA of Formula I, $R_2$, $R_3$ and $R_4$ may independently be a B cell determinant, a T cell determinant, or a targeting molecule. In a preferred embodiment, at least one B cell determinant and one T cell determinant are present in the MAA of Formula I. For example, a monomer MAA of the invention may contain five B cell determinants, two T cell determinants and two targeting molecule side chains. Alternatively, a monomer MAA of the invention may, for example, contain eight B cell determinants, one T cell determinant and one targeting molecule side chain. The combinations are not particularly limited and may vary with the selected B cell determinant, T cell determinant or targeting molecule. Further, the R groups within one Lys-Gly repeat unit, designated by m and n, may vary. For example, if m=3, $R_2$ of the first Lys-Gly repeat may be a B cell determinant, the $R_2$ of the second Lys-Gly repeat may be a T cell determinant and the $R_2$ of the third Lys-Gly repeat may be a targeting molecule.

B cell determinants, as used herein, preferably elicit a measurable B cell response as determined by, for example, production of antibodies to the native viral protein. B cell determinants which may be used in the MAA of Formula I include those already known in the art as well as any other antigens such as glycans, polypeptides, or nucleic acids which elicit a B cell response. In one embodiment, antigens are derived from enveloped or non-enveloped viruses. In another embodiment, antigens are derived from viruses including, but not limited to, those from the family Adenoviridae, Arenaviridae (e.g., Lymphocytic choriomeningitis virus), Arterivirus (e.g., Equine arteritis virus), Astroviridae (Human astrovirus 1), Birnaviridae (e.g., Infectious pancreatic necrosis virus, Infectious bursal disease virus), Bunyaviridae (e.g., California encephalitis virus Group), Caliciviridae (e.g., Caliciviruses), Coronaviridae (e.g., Human coronaviruses 299E and OC43), Deltavirus (e.g., Hepatitis delta virus), Filoviridae (e.g., Marburg virus, Ebola virus Zaire), Flaviviridae (e.g., Yellow fever virus group, Hepatitis C virus), Hepadnaviridae (e.g., Hepatitis B virus), Herpesviridae (e.g., Epstein-Bar virus, Simplexvirus, Varicellovirus, Cytomegalovirus, Roseolovirus, Lymphocryptovirus, Rhadinovirus), Orthomyxoviridae (e.g., Influenzavirus A, B, and C),. Papovaviridae (e.g., Papillomavirus), Paramyxoviridae (e.g., Paramyxovirus such as human parainfluenza virus 1, Morbillivirus such as Measles virus, Rubulavirus such as Mumps virus, Pneumovirus such as Human respiratory syncytial virus), Picornaviridae (e.g., Rhinovirus such as Human rhinovirus 1A, Hepatovirus such Human hepatitis A virus, Human poliovirus, Cardiovirus such as Encephalomyocarditis virus, Aphthovirus such as Foot-and-mouth disease virus O, Coxsackie virus), Poxviridae (e.g., Orthopoxvirus such as Variola virus), Reoviridae (e.g., Rotavirus such as Groups A-F rotaviruses), Retroviridae (Primate lentivirus group such as human immunodeficiency virus 1 and 2), Rhabdoviridae (e.g., rabies virus) and Togaviridae (e.g., Rubivirus such as Rubella virus).

An exemplary B cell determinant which may be used in the MAA of Formula I includes, but is not limited to, M2e or a homolog thereof. In one preferred embodiment, the B cell determinant of the MAA of Formula I is M2e derived from influenza type A. In another embodiment, the B cell determinant is derived from the ectodomain of viral transmembrane proteins such as NB of influenza type B virus or CM2 of influenza type C virus.

T cell determinants are intended to include both Th and cytotoxic T cell determinants. Elicitation of T cell responses may be detected, for example, as exemplified herein or by measuring the production of cytokines, e.g., IFN-gamma, IL-2, IL-4, IL-5, or IL-10. Exemplary T cell determinants which may be used in the MAA of Formula I include, but are not limited to, hemagglutinin T cell determinants and T cell determinants restricted to human MHC class II proteins preferably to a broad range of haplotypes.

Targeting molecules covalently linked to the antigen as the $R_2$, $R_3$, or $R_4$ moieties are, in general, carbohydrates, lipids, peptides or oligonucleotides which deliver the antigen to the desired site. Targeting molecules which may be incorporated into the MAAs of the present invention include, but are not limited to, cholera toxin, ODNs with stimulatory CpG motifs, and endogenous human immunomodulators, such as IL-2, IL-12, and GM-CSF.

The $R_5$ moiety of the MAA of Formula I is not particularly limited and may be any amino acid (e.g., β-linked alanine), peptide, or nucleic acid sequence such as an ODN with a stimulatory CpG motif.

Wherein nucleic acid sequences are incorporated into Formula I, said nucleic acid sequences may be attached via spacer or linker molecules such as hydroxy-carboxylic acid.

The MAA of Formula I may be prepared in accordance with the method exemplified herein or any other suitable method of chemically synthesizing peptides and peptide conjugates.

Examples provided herein disclose various derivatives of the MAA of Formula I for inducing an immune response in mice and are intended to illustrate and not limit the scope of the invention. Other aspects, advantages and modifications within the scope of the invention will be apparent to those skilled in the art to which the invention pertains.

M2e-MAAs were administered to anesthetized mice by the intranasal (i.n.) route in a dose of 50 μl. Primary and booster inocula contained 3 μg of MAA, 3 μg of phosphorothionated oligodeoxynucleotide (ODN) 1826 and 0.5 μg of cholera toxin (CT) in phosphate buffered saline and were given at an interval of four to five weeks. Mice inoculated i.n. with ODN and CT alone or with infectious virus were used as negative and positive controls, respectively. In the latter case, the first infection was with PR8 and the second with PR8-SEQ14, a variant that differs from PR8 by 14 amino acid substitutions in hemagglutinin-determinants recognized by protective monoclonal antibodies and can readily induce an infection in PR8-immune mice.

Ten to thirty days after boost, cells from mediastinal lymph nodes (MedLNs) were tested for their capacity to proliferate in response to free S1 peptide, hemagglutinin and M2e. Cells from spleen and lymph nodes draining the upper respiratory tract gave smaller responses and were less extensively studied. The responses of M2e-MAA-immunized mice consistently exceeded those of adjuvant-primed control mice. Only two of the data sets exceeded the response of the control mice on a statistical basis (paired t test, $p \geqq 0.05$). However, as a group, M2e-MAA-immunized mice exhibited significantly greater S1-and hemagglutinin-specific responses than control mice (unpaired t test, $p \leqq 0.05$). The hemagglutinin-specific response of M2e-MAA-immunized mice was similar in size to the one of infection-immunized mice but differed in fine specificity in that S1-specific Th were detected in M2e-MAA-immunized but not infection-immunized mice. The mannosylated MAA was not superior to non-mannosylated MAAs in inducing a S1-specific Th response in vivo, in marked in contrast to its greater stimulatory potency in vitro. Further, M2e-MAA-immunized but not infection-immunized mice contained M2e-specific proliferative T cells, indicating that M2e itself contains at least one $H2^d$-restricted Th determinant.

There was no evidence of induction of MHC class I-restricted cytotoxic memory T (Tc) responses by M2e-MAAs, which is consistent with the absence of a characteristic $K^d$-restriction, $D^d$-restriction or $L^d$-restriction motif in M2e (Engelhard (1994) *Curr. Opin. Immunol.* 6:13-23; Corr, et al. (1993) *J. Exp. Med.* 178:1877-92). Memory Tc were readily detectable in infection-immunized mice.

M2e-specific serum antibody titers were measured by ELISA on solid phase immunoadsorbents of (1)M2e-MAA and JAP-MDCK cell monolayers. Each assay was standardized and quantified by concomitant titration of purified M2e-specific monoclonal antibody 14C2 and antibody titers in test samples were defined as equivalent μg M2e-specific antibody per milliliter of serum.

Combined data from four independent immunization experiments in which mice were bled 2 and 4 weeks after priming, 2 and 4-5 weeks after second and 2 and 5 weeks after the third immunization provided the average and SEM of group titers from the different immunization experiments. The data indicated that (4)M2e-MAA induced a prompter and stronger response than the (1)M2e-MAAs and the presence of mannose resulted in a further reduction of the antibody response. This held for both the antibody titer measured against (1)M2e-MAA and JAP-MDCK cells. Immunization with (4)M2e-MAA consistently induced significant antibody titers two weeks after the second immunization and sometimes induced a significant response as soon as four weeks after primary immunization (in four independent experiments, mean titers of 1.0, 2.0, 4.6, and 1035 μg/ml 4 weeks after first immunization). The (2)M2e-MAA was included only in two experiments and induced a response that was intermediate between (4)M2e-MAA and (1)M2e-MAA. The findings indicate that a multimeric presentation of M2e enhanced the B cell response, by facilitating the cross-linking of membrane Ig on M2e-specific B cells (Bachmann and Zinkernagel (1997) *Annu. Rev. Immunol.* 15:235-70).

The data further indicated that sera from M2e-MAA-immunized mice consistently exhibited higher titers against M2e-MAA than against JAP-MDCK cells. The ratio of M2e-MAA versus JAP-MDCK reactive antibodies in sera showed an average of 10 and ranged in individual sera from two to 31. This indicates that the specificity of the antibody response after M2e-MAA immunization differed amongst individual mice and that on average ~10% of the M2e-MAA specific antibodies cross-reacted with virus-induced M2e on infected cells. The residual antibodies may be directed to Th-determinants, scaffold peptide, determinants on the synthetic M2e-peptide that are not shared by the virus-induced M2-tetramer or combinations of these structures.

ELISA against M2e-MAA further indicated that sera from virus-infected mice contained very low M2e-specific antibody titers. The ELISA against JAP-MDCK detects antibodies to many viral proteins and was therefore not used to quantify the M2-specific response in infection-immunized mice. The only exception was one group of mice that had been immunized by three consecutive infections, first by PR8, second by JAP and third by X31 and exhibited a M2e-MAA-specific titer of ~30 μg/ml, which was in the same range as the viral M2e-specific antibody titers (versus JAP-MDCK) seen in (4)M2e-MAA-immunized mice. The data showed that (4)M2e-MAA was more effective than virus infection in inducing a M2e-specific antibody response.

M2e-specific immune effectors were virtually absent from mice immunized by two consecutive infections. This is surprising, considering that M2 is expressed at high density in the plasma membrane of infected cells (Lamb, et al. (1985) supra; Zebedee and Lamb (1988) supra) and that a vast number of epithelial cells become infected in the course of a total respiratory tract infection (Yilma, et al. (1979) *J. Inf. Disease* 139:458-64). This finding indicates that the strength of heterosubtypic protection may be enhanced by concomitant induction of the effectors induced by infection and M2e-specific vaccination.

Four to five weeks after the second immunization, mice were challenged with X31 and virus titer in nasal, tracheal and pulmonary tissues determined three days later. Mice immunized with MAAs that contained a single M2e, with or without mannose, exhibited no significant resistance (ns, p>0.01 by student t test) to virus replication in nasal and pulmonary tissues but showed reduced virus replication in the trachea compared to mice primed with adjuvant alone. By contrast, mice immunized with (4)M2e-MAA showed reduced virus growth in all parts of the respiratory tract. Compared with infection-immunized mice, the resistance in (4)M2e-MAA-immune mice was of similar strength in nasal and tracheal tissues but of lower strength in pulmonary tissue.

M2e-specific serum antibody titers were tested in individual mice for correlation with virus titers. Antibody titers and nasal and pulmonary, but not tracheal, virus titers correlated inversely in (4)M2e-MAA-immunized mice (correlation coefficient, $R^2$, for nose and lung 0.53 and 0.51, respectively, p<0.001). However, a substantial fraction of the correlation was due to the single, outlying mouse that contained ~90 pg anti-M2e antibody per ml of serum. Its exclusion reduced the correlation between antibody and virus titer to an insignificant value in the nose but not in the lung, where it remained significant ($R^2$ 0.41, p=0.002). No correlation was seen between M2e-specific antibody and virus titers in trachea and in mice immunized by infection.

Given these results, another aspect of the present invention provides the use of MAAs both as therapeutic and prophylactic agents for treating or preventing viral infections. In general, this will involve administering an effective amount of one or more MAAs of the present invention in a suitable form to a susceptible subject or one exhibiting signs or symptoms of viral infection.

As will be appreciated by the skilled artisan, the selection of the B cell determinant for the MAA of Formula I will be dependent on the viral infection to be prevented or treated. For example, to prevent or treat an influenza viral infection, the B cell determinant of the MAA of Formula I should be derived from influenza virus (e.g., M2e). In using cognate B cell determinants, it is contemplated that the MAA of Formula I will be effective in generating an immune response against enveloped or non-enveloped viruses including, but not limited to, those from the family Adenoviridae, Arenaviridae (e.g., Lymphocytic choriomeningitis virus), Arterivirus (e.g., Equine arteritis virus), Astroviridae (Human astrovirus 1), Birnaviridae (e.g., Infectious pancreatic necrosis virus, Infectious bursal disease virus), Bunyaviridae (e.g., California encephalitis virus Group), Caliciviridae (e.g., Caliciviruses), Coronaviridae (e.g., Human coronaviruses 299E and OC43), Deltavirus (e.g., Hepatitis delta virus), Filoviridae (e.g., Marburg virus, Ebola virus Zaire), Flaviviridae (e.g., Yellow fever virus group, Hepatitis C virus), Hepadnaviridae (e.g., Hepatitis B virus), Herpesviridae (e.g., Epstein-Bar virus, Simplexvirus, Varicellovirus, Cytomegalovirus, Roseolovirus, Lymphocryptovirus, Rhadinovirus), Orthomyxoviridae (e.g., Influenzavirus A, B, and C), Papovaviridae (e.g., Papillomavirus), Paramyxoviridae (e.g., Paramyxovirus such as human parainfluenza virus 1, Morbillivirus such as Measles virus, Rubulavirus such as Mumps virus, Pneumovirus such as Human respiratory syncytial virus), Picornaviridae (e.g., Rhinovirus such as Human rhinovirus 1A, Hepatovirus such Human hepatitis A virus, Human poliovirus, Cardiovirus such as Encephalomyocarditis virus, Aphthovirus such as Foot-and-mouth disease virus O, Coxsackie virus), Poxviridae (e.g., Orthopoxvirus such as Variola virus), Reoviridae (e.g., Rotavirus such as Groups A-F rotaviruses), Retroviridae (Primate lentivirus group such as human immunodeficiency virus 1 and 2), Rhabdoviridae (e.g., rabies virus) and Togaviridae (e.g., Rubivirus such as Rubella virus).

Treatment of individuals having a viral infection involves identifying a subject exhibiting signs or symptoms of a viral infection and administering to said subject an effective amount of a MAA of Formula I of the present invention. Signs or symptoms of a viral infection are generally dependent on the particular virus and are well-known to the skilled clinician. For example, typical symptoms of viral infection include, but are not limited to high fever, severe aches and pains, headaches, and sore throat. MAAs for treating viral infections may be used or administered as a mixture, for example in equal amounts, or individually, provided in sequence, or administered all at once and may be administered orally, topically or parenterally in amounts sufficient to effect a reduction in the viral infection signs or symptoms. Further, the MAAs of the present invention may be co-administered with other well-known antigens, vaccines or adjuvants.

Likewise, active immunization for the prevention or protection against a viral infection involves administering one or more MAAs as a component of a vaccine. Vaccination may be performed orally, topically or parenterally in amounts sufficient to enable the recipient subject to generate protective immunity against the virus of interest to prevent the signs or symptoms of viral infection. An amount is said to be sufficient to prevent the signs or symptoms of viral infection if the dosage, route of administration, etc. of the MAA are sufficient to influence such a response. Responses to MAA administration may be measured by analysis of subject's vital signs.

An MAA composition suitable for administration is one which is tolerated by a recipient subject. Such MAA compositions may be prepared according to known methods of producing formulations, whereby the MAAs are combined in admixture with a pharmaceutically acceptable carrier. Pharmaceutically acceptable carriers are provided, for example, in Remington: The Science and Practice of Pharmacy, Alfonso R. Gennaro, editor, 20th ed. Lippingcott Williams & Wilkins: Philadelphia, Pa., 2000. In order to form an MAA composition suitable for administration, such compositions will contain an effective amount of the MAAs together with a suitable amount of a carrier, excipient, or stabilizer which is nontoxic to the cell or mammal being exposed thereto at the dosages and concentrations employed. In general, formulations will contain a final concentration of MAA in the range of 0.2 µg/ml to 2 µg/ml, preferably 5 µg/ml to 500 µg/ml, most preferably about 100 µg/ml. Often the carrier is an aqueous pH buffered solution. Examples of pharmaceutically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

MAAs, or compositions or formulations containing an MAA of the invention may further contain adjuvants to enhance a subject's T cell response to the antigen. Examples of such adjuvants include, but are not limited to, aluminum salts; Incomplete Freund's adjuvant; threonyl and n-butyl derivatives of muramyl dipeptide; lipophilic derivatives of muramyl tripeptide; monophosphoryl lipid A; 3'-de-O-acetylated monophosphoryl lipid A; cholera toxin; phosphorothionated oligodeoxynucleotides with CpG motifs; and adjuvants such as those disclosed in U.S. Pat. No. 6,558,670.

Administration of MAAs, or compositions or formulations containing an MAA disclosed herein may be carried out by any suitable means, including parenteral injection (such as intraperitoneal, subcutaneous, or intramuscular injection), orally, or by topical application of the MAAs (typically carried in a pharmaceutical formulation) to an airway surface. Topical application of the MAAs to an airway surface may be carried out by intranasal administration (e.g., by use of dropper, swab, or inhaler which deposits a pharmaceutical formulation intranasally). Topical application of the MAAs to an airway surface can also be carried out by inhalation administration, such as by creating respirable particles of a pharmaceutical formulation (including both solid particles and liquid particles) containing the MAAs as an aerosol suspension, and then causing the subject to inhale the respirable particles. Methods and apparatus for administering respirable particles of pharmaceutical formulations are well-known, and any conventional technique may be employed.

Oral administration may be in the form of solutions, suspensions, tablets, pills, capsules, sustained release formulations or powders and contain 10% to 95% of active ingredient, preferably 25% to 70%. Capsules, tablets and pills for oral administration to a subject may be provided with an enteric coating comprising, for example, copolymers of methacrylic acid and methyl methacrylate, cellulose acetate, cellulose acetate phthalate or hydroxypropylmethyl cellulose.

A composition of the invention may be administered in a manner compatible with the dosage formulation, and in such amount as will be prophylactically and/or therapeutically effective. The quantity to be administered, which is generally in the range of 5 μg to 250 μg of MAA per dose, depends on the subject to be treated, capacity of the subject's immune system to synthesize antibodies, and the degree of protection desired. A preferable range is from about 15 μg to about 50 μg per dose.

A suitable dose size is about 0.5 ml. Accordingly, a dose for intramuscular injection, for example, would comprise 0.5 ml containing 20 μg of MAA in admixture with 0.5% adjuvants.

The exact dosage will be determined by the skilled practitioner, in light of factors related to the subject that requires treatment. Dosage and administration are adjusted to provide sufficient levels of the active MAA or to maintain the desired effect of preventing or reducing viral signs or symptoms, or reducing severity of the viral infection. Factors which may be taken into account include the severity of the disease state, general health of the subject, age, weight, and gender of the subject, diet, time and frequency of administration, drug combination(s), reaction sensitivities, and tolerance/response to therapy.

The composition may be given in a single dose schedule, or preferably in a multiple dose schedule. A multiple dose schedule is one in which a primary course of administration may be with 1-10 separate doses, followed by other doses given at subsequent time intervals required to maintain and or reinforce the immune response, for example, at 1 to 4 months for a second dose, and if needed, a subsequent dose(s) after several months. The dosage regimen will also, at least in part, be determined by the need of the individual and be dependent upon the judgement of the practitioner.

The invention is described in greater detail by the following non-limiting examples.

EXAMPLE 1

Synthesis of Multiple Antigenic Agent Constructs (MAAs)

The solid-phase synthesis of multivalent mannosylated (1)M2e-Man-MAA consisting of:

```
Man
 |
Ser
 |
Lys-Gly-Lys-Gly-Lys-Gly-Lys-Gly-Lys-Gly-Lys-Gly-β-Ala
 |       |       |       |       |       |
Ser     Ser     Ser      S2      S1      M2e
 |       |       |
Man     Man     Man
```

(SEQ ID NO:2) and non-mannosylated peptide constructs (1)M2e-MAA consisting of:

```
Lys-Gly-Lys-Gly-Lys-Gly-Lys-Gly-Lys-Gly-Lys-Gly-β-Ala
 |       |       |       |       |
Ser     Ser      S2      S1      M2e
```

(SEQ ID NO:3) and (2)M2e-MAA consisting of:

```
Ser
 |
Cys-Gly-Lys-Gly-Lys-Gly-Lys-Gly-Lys-Gly-β-Ala
 |       |       |       |       |
Ser      S2      S1      M2e     M2e
```

(SEQ ID NO:4) with the use of a combination of three quasi-orthogonally removable amino protecting groups was performed using well-known methods (Kragol and Otvos (2001) *Tetrahedron* 57:957-66). The disulfide-linked octameric peptide construct (4)M2e-MAA consisting of:

```
Cys-Gly-Lys-Gly-Lys-Gly-Lys-Gly-Lys-Gly-β-Ala
 |       |       |       |       |
 S       S2      S1      M2e     M2e
 |
 S
 |
```

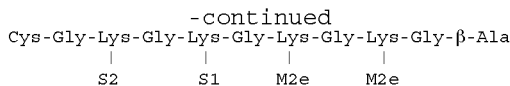
(SEQ ID NO:5) carrying four copies of M2e as well as two copies each of helper T cell determinants S1 and S2, was made via intermolecular disulfide formation from free sulfhydryl-bearing cysteine derivatives in solution (Kragol, et al. (2001) *Bioorg. Med. Chem. Lett.* 11:1417-20). Peptide constructs Cys-backbone consisting of:
Cys-Gly-Lys-Gly-Lys-Gly-Lys-β-Ala (SEQ ID NO:6)
and
Cys-M2e consisting of:
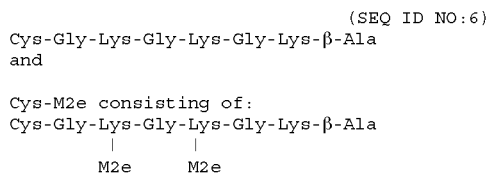
(S reagents were diluted in PBSN containing 1% BSA, used at 25 µl/round-bottom well or 50 µl/flat-bottom well, and incubated for 90 minutes at room temperature. Bound mouse antibody was generally detected with biotinylated rat-anti-mouse-Cκ monoclonal antibody 187.1, followed by Streptavidin-AP (Sigma, St. Louis, Mo.) and pNPP (Sigma, St. Louis, Mo.). The pNPP solution was used at 50 µl and 100 µl per round- and flat-bottom well, respectively. Absorption was measured with the EMAX® plate reader (Molecular Devices, Sunnyvale, Calif.) and the difference between $OD_{405}$ and $OD_{750}$ ($OD_{405-750}$) recorded, usually after 30-45 minute of incubation. All assays included a titration of a purified monoclonal antibody of appropriate specificity for quantification of test samples. ELISA data were analyzed with the SOFTMAX PRO® software (Molecular Devices, Sunnyvale, Calif.).

EXAMPLE 6

Analysis of CD4+ T Cell Responses

Antigen presenting cells (APC) were prepared from the spleen of naïve BALB/c mice. PERCOLL™ (PHARMACIA®, Uppsala, Sweden) was added to the cell suspension to give a final concentration of 33%. The suspension was underlayed with a small volume of 70% PERCOLL™ and centrifuged (10 minutes, 600 g, room temperature) to remove cell debris and erythrocytes. Cells at the 33%/70% interface were harvested, washed, irradiated (2200 rad) and suspended in ISC-CM at $5\times10^6$ cells/ml. One hundred µl were dispensed per well of flat-bottomed tissue culture plates. Antigen in ISC-CM was added in 50 µl volumes per well. Fifty µl of responder cell suspension, typically MedLN cells at $10^7$/ml or Th clones at $4\times10^5$/ml in ISC-CM, were added per well. One µCi of $H^3$-thymidin was added during the third (Th clones) or fourth (LN responder cells) day of incubation. Plates were then frozen and thawed once and the cells were harvested with a Skatron cell harvester (Skatron Instruments Inc., Sterling, Va.) onto filter mats (Skatron Instruments Inc., Sterling, Va.). Punched out pieces of filter mat were transferred into scintillation fluid and counted for radioactivity.

EXAMPLE 7

Analysis of CD8+ Memory T Cell Response

Spleen cells from vaccinated mice were purified as provided in a 33%/70% PERCOLL™ gradient and used as responder cells. A20 cells ($H2^d$, positive for MHC class II) were infected with PR8 ($10^6$ $TCID_{50}/10^6$ A20, one hour at 37° C.), irradiated with 4400 rad, washed and used as stimulators. Cultures (6 ml) were set up in T25 Falcon flasks and contained $25\times10^6$ responder cells and $10^6$ stimulator cells in ISC-CM containing 5% FCS. After five days of incubation (stationary, upright), viable cells were purified in a 33%/70% PERCOLL™ gradient, counted and using standard methods (Mozdzanowska, et al. (1997) *Virology* 15 239:217-25) tested for the ability to induce release of $^{51}Cr$ from PR8- and B/LEE-infected P1.HTR target cells during a four hour incubation period.

EXAMPLE 8

Immunization Protocols

M2e-MAAs and adjuvants, in a total volume of 50 µl, were placed onto the nares of anesthetized mice (ketamine and xylazine injected intraperitoneally at 70 mg/kg and 7 mg/kg body weight, respectively), which resulted in its aspiration into the respiratory tract. One dose of 50 µl contained 3 µg of M2e-MAA, 3 µg of the ODN 1826 (Krieg, et al. (1995) *Nature* 374:546-9; Yi, et al. (1998) *J. Immunol.* 160:4755-61) and 0.5 µg of CT (Sigma, St. Louis, Mo.). Adjuvant combination and dosing was based on standard methods (Mozdzanowska, et al. (1999) supra). Booster inoculations were administered in four to five week intervals. Mice that received adjuvant solution without M2e-MAA were used as negative controls and mice that had been subjected to two consecutive respiratory tract infections, first with PR8 and second with PR8-SEQ 14, were used as positive controls.

EXAMPLE 9

Virus Challenge Experiments

The strength of vaccine-induced protection was tested by i.n. challenge of mice with ~$10^3$ $MID_{50}$ (50% mouse infectious dose) of X31. Three days later, the mice were anesthetized, exsanguinated by heart puncture, and dissected for collection of nasal, tracheal and pulmonary tissues. Titers of infectious virus were determined by titration of tissue homogenates in MDCK cell cultures or embryonated hen's eggs using standard methodologies (McCluskie and Davis (2000) supra).

EXAMPLE 10

In Vitro Analysis of Immune Response to MAAs

To induce a Th-dependent antibody response to native viral M2e, M2e-MAAs shared B cell epitopes with native virus-induced M2e and contained determinants that could be presented to Th cells. JAP-MDCK cells and M2e-MAAs were compared for their reaction with several M2e-specific monoclonal antibodies in ELISA. The 14C2 monoclonal antibody was generated from a mouse immunized with purified viral M2 (Zebedee and Lamb (1988) supra); all other antibodies were isolated from mice recovered from consecutive influenza type A virus infections and boosted with (4)M2e-MAA three days prior to fusion. The final boost with (4)M2e-MAA was performed to increase the frequency of isolation of M2e-specific hybridomas. All six M2e-specific monoclonal antibodies reacted well with both M2e-MAA and JAP-MDCK, though four were slightly more and two slightly less effective in binding to JAP-MDCK than to wells coated with (1)M2e-MAA at 1.5 ng/well. The data indicated that M2e-MAAs mimicked effectively several B cell determinants of the native virus-induced tetrameric M2e.

The structurally different M2e-MAAs, when used at equimolar M2e concentrations, showed no significant differences in reaction with M2e-specific monoclonal antibodies.

To optimize Th-mediated help, two distinct Th determinants were incorporated into the MAAs, one (S1) presented by $E^d$ and the other (S2) by $A^d$. These determinants were identified as the two immunodominant targets of the HA(PR8)-specific Th response of BALB/c ($H-2^d$) mice (Gerhard, et al. (1991) *J. Virol.* 65:364-72). S1 corresponds to the HA region 110-120 and S2 to 126-138. However, the S2 peptide in the present constructs was altered compared to the native S2 by replacing the cysteine at position 135 with serine to avoid formation of disulfide bonds between S2 and the cysteine contained in the M2e peptide.

The efficacy of the MAAs to stimulate S1- and S2-specific Th clones was determined in cultures that contained irradiated BALB/c spleen cells as APCs, S1- or S2-specific Th clones as responders and various concentrations of free S1 or S2 peptides, M2e-MAAs or purified HA. Proliferation of the Th clones was assessed by $^3$H-thymidine incorporation during the third day of culture. All M2e-MAAs stimulated the S1-specific Th clone V2.1 with equal or higher potency than the free S1 peptide. A 100-fold greater stimulatory potency of the mannosylated MAA was observed most likely due to improved capture of this MAA by mannose-receptors expressed on APCs (Engering, et al. (1997) *Eur. J. Immunol.* 27:2417-2; Tan, et al. (1997) *Eur. J. Immunol.* 27:2426-35). The stimulatory activity of this MAA is similar, on a molar basis, to the activity of the HA molecule which also contains mannosylated carbohydrate side chains (Keil, et al. (1985) *EMBO J.* 4:2711-20).

By contrast, none of the MAAs stimulated the S2-specific Th clone 5.1-5R6. This Th clone responded well to stimulation with the isolated native S2 peptide and intact HA, thus the change of Cys(135) to Ser may have reduced its stimulatory potency for this Th clone. Two additional, clonally unrelated, S2-specific Th clones were tested and also failed to respond to MAAs. Since the Cys(135)→Ser does not to affect the peptide's ability to bind to $A^d$ (Sette, et al. (1989) *J. Immunol.* 142:35-40), it may form an antigenically novel Th determinant which is not recognized by Th specific for the native S2 determinant. Crystal structure analysis of the S2/$A^d$ complex indicated that the amino acid at position 135 is not an anchor residue (Scott, et al. (1998) *Immunity* 8:319-29).

Thus, the in vitro analyses indicated that the M2e-MAAs mimicked B cell determinants of the native virus-induced M2e and contained at least one functional Th determinant.

What is claimed is:

1. A multiple antigenic agent comprising:

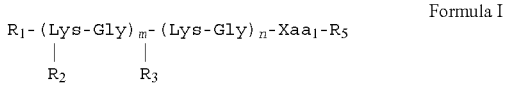

Formula I (SEQ ID NO:1) wherein, $R_1$ is 0 to 2 amino acid residues comprising Cys or Gly or a nucleic acid sequence; m is at least 1; n is at least 1; $R_2$ and $R_3$ are independently a B cell determinant, a T cell determinant, or targeting molecule; and $R_5$ is alanine.

2. The multiple antigenic agent of claim 1, wherein the B cell determinant comprises the ectodomain of matrix protein 2 or a homolog thereof.

3. The multiple antigenic agent of claim 1, wherein the $R_1$ of a first and second multiple antigenic agent is Cys-Gly and said Cys residue of said first and second multiple antigenic agent are covalently linked to produce a dimer.

4. A composition comprising the multiple antigenic agent of claim 1 and a pharmaceutically acceptable carrier.

5. The composition of claim 4, wherein the composition further comprises an adjuvant.

6. The composition of claim 4, wherein the composition comprises a vaccine.

7. The composition of claim 5, wherein the composition comprises a vaccine.

8. A method for preventing or treating a viral infection comprising administering to a subject an effective amount of a composition of claim 4 to prevent or treat the signs or symptoms of a viral infection.

9. A method for preventing or treating a viral infection comprising administering to a subject an effective amount of a composition of claim 5 to prevent or treat the signs or symptoms of a viral infection.

10. A method for preventing or treating a viral infection comprising administering to a subject an effective amount of a composition of claim 6 to prevent or treat the signs or symptoms of a viral infection.

11. A method for preventing or treating a viral infection comprising administering to a subject an effective amount of a composition of claim 7 to prevent or treat the signs or symptoms of a viral infection.

12. The method of claim 8, wherein the viral infection comprises influenza type A virus.

13. The method of claim 9, wherein the viral infection comprises influenza type A virus.

14. The method of claim 10, wherein the viral infection comprises influenza type A virus.

15. The method of claim 11, wherein the viral infection comprises influenza type A virus.

* * * * *

UNITED STATES PATENT AND TRADEMARK OFFICE
CERTIFICATE OF CORRECTION

PATENT NO. : 7,527,798 B2
APPLICATION NO. : 10/541771
DATED : May 5, 2009
INVENTOR(S) : Gerhard et al.

It is certified that error appears in the above-identified patent and that said Letters Patent is hereby corrected as shown below:

At Column 21 in Claim 1:

Please delete:
A multiple antigenic agent comprising:

and insert:
A multiple antigenic agent comprising:

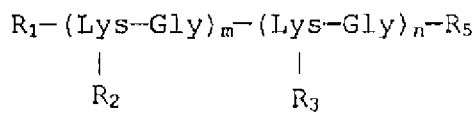

The reference to $R_3$ should be under Lys, not under m.

Signed and Sealed this

Ninth Day of June, 2009

JOHN DOLL
*Acting Director of the United States Patent and Trademark Office*